United States Patent [19]

Steenbergen et al.

[11] Patent Number: 4,689,160

[45] Date of Patent: Aug. 25, 1987

[54] ACID STABLE HETEROPOLYSACCHARIDE S-421

[75] Inventors: Suzanne M. Steenbergen, Alpine; Glen H. Best, Carlsbad, both of Calif.

[73] Assignee: Merck & Co., Inc., Rahway, N.J.

[21] Appl. No.: 819,447

[22] Filed: Jan. 16, 1986

[51] Int. Cl.[4] .......................... E21B 43/27; C12P 19/06
[52] U.S. Cl. .................. 252/8.553; 166/307; 252/315.3; 435/104; 435/822; 536/114
[58] Field of Search ...................... 252/8.55 C, 8.553; 166/307, 282; 536/114; 435/104

[56] References Cited

U.S. PATENT DOCUMENTS

| | | |
|---|---|---|
| 3,236,305 | 2/1966 | Parks . |
| 4,186,025 | 1/1980 | Kang et al. .................. 252/8.55 X |
| 4,244,826 | 1/1981 | Swanson . |
| 4,259,451 | 3/1981 | Steenbergen et al. . |
| 4,269,939 | 5/1981 | Kang et al. . |
| 4,339,239 | 7/1982 | Racciato . |
| 4,342,866 | 8/1982 | Kang et al. .................. 252/8.55 X |
| 4,529,797 | 7/1985 | Peik et al. ..................... 536/123 |
| 4,574,050 | 3/1986 | Crowe et al. ................. 252/8.55 |

OTHER PUBLICATIONS

Carbohydrate Research, 61 (1978) 89–96 Makoto Hisamatsu, et al. Acidic Polysaccharides Containing Succinic Acid in Various Strains of Agrobacterium.
Derwent Abstract 74882j.
Carbohydrate research, 26 (1973) 409–419, Methylation Analysis of Acidic Exopolysaccharides of Rhizobium and Agrobacterium.
Carbohydrate Research, 77 (1979) 285–288, Comparative Studies of Polysaccharides Eleborated by Rhizobium, Alcaligenes and Agrobacterium.
Biochimica et Biophysica Acta, 585 (1979) 611–619, Preliminary Studies on the Composition and Rheological Properties of the Extracellular Polysaccharide Synthesized by Pseudomonas PB1 (NCIB 11264).

*Primary Examiner*—Herbert B. Guynn
*Attorney, Agent, or Firm*—Gabriel Lopez; Charles M. Caruso; Hesna J. Pfeiffer

[57] ABSTRACT

Heteropolysaccharide S-421, prepared by fermentation of an unidentified Agrobacterium species ATCC 53378, has valuable properties as an acid stable heteropolysaccharide and is especially valuable for use in acidizing fluids.

5 Claims, No Drawings

ACID STABLE HETEROPOLYSACCHARIDE S-421

BACKGROUND OF THE INVENTION

This invention pertains to the field of microbial polysaccharides. In this field it is known that a common feature of certain microorganisms is the production of exocellular heteropolysaccharides. Heteropolysaccharides are high molecular weight generally linear carbohydrate polymers containing two or more kinds of monosaccharides that form a repeating unit that is polymerized.

Heteropolysaccharides are widely used in food, well drilling, agricultural and a wide variety of other industrial applications. Commercial demand for these water soluble gums has greatly increased over the last few decades. Furthermore, new industrial techniques create a need for heteropolysaccharides with new physical properties. Consequently, the need for heteropolysaccharides with different functionalities, coupled with commercial demand, has clearly indicated the necessity for the development of new heteropolysaccharides with new and different physical properties.

Acid stable heteropolysaccharides are of interest in oilfield applications, particularly in production enhancement operations. Enhancement of recovery of oil and gas from underground reservoirs can be accomplished by various stimulation techniques. One technique that has been widely employed is known as "acidizing". This technique comprises introducing an acid, preferably a non-oxidizing acid, into the well under sufficient pressure to force the acid out into the underground formation where it reacts with the acid soluble components of the formation such as, for example, limestones, dolomites and sandstones containing streaks of carbonates. During acidizing, passageways for fluid flow within the formation are created or existing passageways are enlarged, thus increasing the porosity and permeability of the formation and, therefore, increasing oil and gas production from the underground reservoir.

The heteropolysaccharide produced by *Xanthomonas campestris* (xanthan gum) which contains glucose, mannose and glucuronic acid has found wide use in secondary oil recovery applications. In U.S. Pat. No. 3,236,305, a method of acidizing wells utilizing xanthan gum is shown. In U.S. Pat. No. 4,244,826, xanthan gum is also shown for use in gelled acidic well treating compositions.

Organisms classified as *Agrobacterium radiobacter* IFO (Institute of Fermentation, Osaka) 12607, IFO 12664, IFO 12665, IFO 13127, IFO 13256, IFO 13532 and IFO 13533 have been used to produce exocellular polysaccharides (Hiramatsu, et al., "Acidic Polysaccharides Containing Succinic Acid in Various Strains of Agrobacterium", Carbohydrate Research, (1978) 61, 96–98. These organisms were grown in a synthetic medium described in Amemura, et al., Hakko Kogaku Zasshi; (1971) 49, 559–564, Chem. Abst. 75, 1971, 74882j.

An exopolysaccharide containing D-glucose, D-galactose, pyruvic acid, and O-acetyl groups in the approximate proportions 6:1:1:1.5 is described by L. Zevenhuizen, "Methylation Analysis of Acidic Exopolysaccharides of Rhizobium and Agrobacterium", Carbohydrate Research, (1973) 26, 409–419. The organisms used by Zevenhuizen are described as *Agrobacterium tumefaciens* A-8 and A-10.

The organisms *Agrobacterium radiobacter* (IFO 12665) has been used to produce polysaccharides having a similar structure to that reported by Zevenhuizen (T. Harada, et al., "Comparative Studies of Polysaccharides Elaborated by *Rhizobium, Alcaligenes,* and *Agrobacterium*", Carbohydrate Research, (1979) 77, 285–288). Additionally, the polysaccharide isolated from a *Pseudomonas* organism reported in A. G. Williams, et al., "Preliminary Studies on the Composition and Rheological Properties of the Extracellular Polysaccharide Synthesized by Pseudomonas PB1 (NCIB 11264)", Biochem. Biophys. Acta, 585 (4) 611–619 (1979) has a similar structure.

U.S. Pat. Nos. 4,259,451; 4,269,939 and 4,339,239 disclose a heteropolysaccharide for use in the control of color migration during dying of fabrics which has a composition similar to those described above.

It is an object of the present invention to provide an improved acid stable heteropolysaccharide which is produced by an unidentified *Agrobacterium* species. It is also an object of this invention to provide a heteropolysaccharide which thickens acid solutions, particularly hydrochloric acid solutions, containing high acid concentrations. It is an additional object of the present invention to provide an improved acidizing fluid composition with enhanced acid stability. It is still another object of this invention to provide a method for making this acid stable heteropolysaccharide. A still further object is to provide microorganisms for making the improved heteropolysaccharide. These and other objects of the invention will become apparent from the ensuing description.

SUMMARY OF THE INVENTION

It has now been found that an unidentified *Agrobacterium* species produces an acid stable heteropolysaccharide when incubated in a selected nutrient medium. A deposit under the Budapest Treaty of a biologically pure culture of this organism was made with the American Type Culture Collection, Rockville, Md., on Dec. 19, 1985 under Accession No. ATCC 53378. The acid stable heteropolysaccharide S-421 is prepared by growing the *Agrobacterium species* ATCC 53378 in an aqueous nutrient medium by aerobic fermentation of an assimilable carbon source and then recovering said heteropolysaccharide S-421. The assimilable carbon source is a carbohydrate, particularly glucose.

This heteropolysaccharide has desireable properties in aqueous acid systems and is especially useful in formulating aqueous acidizing fluids. Such aqueous acidizing fluids contain from about 6 to about 35% by weight acid and from about 0.1 to 2.0% by weight heteropolysaccharide, said heteropolysaccharide containing principally carbohydrate, about 12% by weight protein, about 4% by weight acyl groups principally as O-succinyl groups, and about 4% by weight pyruvate, said carbohydrate portion containing the neutral sugars glucose and galactose in the approximate molar ratio of 6:1. The acids preferred for use in said acidizing fluids are non-oxidizing acids, selected from the group consisting of hydrochloric acid, hydrofluoric acid, acetic acid or formic acid, or combinations thereof.

DETAILED DESCRIPTION OF THE INVENTION

The organism used in the present invention was isolated from a water sample taken from Douglas Lake east of Knoxville, Tenn. The organism was picked as a gummy colony from a 1% glucose (Difco) agar plate after 4 days of incubation at 30° C. The isolate was then pure cultured on nutrient agar. A flask seed was started from a nutrient agar culture of the isolate. This seed was then used to inoculate another flask containing a nutrient medium having hydrolyzed starch as the carbon source. After incubation, this flask was noted to contain a viscous beer and upon addition of isopropyl alcohol a fibrous material was precipitated. Another flask seed was started and used to determine the effect of various nutrient media on gum production and to determine the best growth media and fermentation conditions for this microorganism.

FERMENTATION CONDITIONS

Heteropolysaccharide S-421 is produced during the aerobic fermentation of suitable aqueous nutrient media under controlled conditions via inoculation with a culture of the organism ATCC 53378, also referred to herein as S-421. The media contain sources of assimilable carbon, nitrogen, and inorganic salts.

In general, carbohydrates (for example, glucose, fructose, maltose, sucrose, xylose, lactose and the like) can be used either alone or in combination as sources of assimilable carbon in the nutrient medium. The exact quantity of the carbohydrate source or sources utilized in the medium depends in part upon the other ingredients of the medium but, in general, the amount of carbohydrate usually varies between about 2% and 5% by weight of the medium. These carbon sources may be used individually or combined in the medium.

Generally, many proteinaceous materials may be used as nitrogen sources for the fermentation process. Suitable nitrogen sources include, for example, yeast hydrolysates, primary yeast, soybean meal, cottonseed flour, hydrolysates of casein, cornsteep liquor, distiller's solubles or tomato paste and the like. The sources of nitrogen, either alone or in combination, are used in amounts preferably ranging from about 0.05% to 0.2% by weight of the aqueous medium.

Among the nutrient inorganic salts which can be incorporated in the culture media are the customary salts capable of yielding sodium, potassium, ammonium, calcium, phosphate, sulfate, chloride, carbonate, and the like ions. Also included are trace metals such as cobalt, manganese, iron and magnesium.

It should be noted that the nutrient media described herein are merely illustrative of the wide variety of media which may be employed, and are not intended to be limiting.

As an alternate medium, S-421 may be grown under low calcium ion conditions, i.e., in deionized water or some other aqueous system substantially free of calcium ions (i.e., less than about 4 ppm $Ca^{++}$ per 1% gum in the final fermentor broth).

The fermentation is carried out at temperatures ranging from about 25° C. to 35° C.; however, for optimum results it is preferable to conduct the fermentation at temperatures of from about 28° C. to 32° C. The pH of the nutrient media for growing the ATTC 53378 culture and producing the heteropolysaccharide S-421 can vary from about 6 to 8.

Although S-421 is produced by both surface and submerged culture, it is preferred to carry out the fermentation in the submerged state.

A small scale fermentation is conveniently carried out by inoculating a suitable nutrient medium with the culture and, after transfer to a production medium, permitting the fermentation to proceed at a constant temperature of about 30° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 30° C. for 1-2 days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flasks are recovered by precipitation with a suitable alcohol such as isopropanol.

For large scale work, it is preferable to conduct the fermentation in suitable tanks provided with an agitator and a means of aerating the fermentation medium. According to this method, the nutrient medium is made up in the tank and sterilized by heating at temperatures of up to about 121° C. Upon cooling, the sterilized medium is inoculated with a previously grown seed of the producing culture, and the fermentation is permitted to proceed for a period of time as, for example, from 2 to 4 days while agitating and/or aerating the nutrient medium and maintaining the temperature at about 30° C. This method of producing S-421 is particularly suited for the preparation of large quantities.

HETEROPOLYSACCHARIDE S-421

The heteropolysaccharide produced by ATCC 53378 is composed principally of carbohydrate, about 12% by weight protein, about 4% by weight (calculated as acetic acid) acyl groups principally as O-succinyl groups, and about 4% by weight pyruvate. The carbohydrate portion of S-421 contains the neutral sugars glucose (84-92%; 85% ave.) and galactose (8-16%; 15% ave.) in the approximate molar ratio of 6:1.

The acyl content of about 4% was determined by two separate techniques. A 0.2% aqueous solution of S-421 gum was treated with an alkaline, hydroxylamine reagent followed by treatment with an acidic ferric chloride reagent and colorimetric analysis [See. S. Hestrin (1949) *J. Biol. Chem.* 180, 249-261]. The O-acyl group was also quantitated by liquid chromatography and identified as O-succinyl.

The neutral sugars of S-421 were also determined by various techniques. One method involves hydrolyzing 50 mg of S-421 in 1 ml of 1M $H_2SO_4$ at 100° C. for 4 hours. In the second method the sample was digested in 72% $H_2SO_4$ at 0° C. for 1 hour and then hydrolyzed in 1M $H_2SO_4$ for 4 hours at 100° C. The sugars were separated by gas-liquid chromatography of their aldononitrile acetate derivatives and were identified and quantified by comparison with authentic standards [J. K. Baird, M. J. Holroyde, and D. C. Ellwood (1973) *Carbohydr. Res.* 27, 464-467].

Pyruvate was determined by the method of Duckworth and Yaphe *Chem. and Ind.* (1970) p. 747.

The protein content was determined by the method of Lowry et al., [*J. Biol. Chem.*, (1951), 193, p. 256] using bovine serum albumin as standard.

It is to be understood that, although the methods of analysis of the heteropolysaccharide described herein were the actual methods used in arriving at the composition described above, other methods of analysis are available to one skilled in the art. Utilization of other methods of analysis should result in the same characterization of the heteropolysaccharide, however, slightly different quantitative results may be reported.

Heteropolysaccharide S-421 has been found to have outstanding properties in aqueous solution, especially in having very high viscosity at very low concentrations and excellent stability in highly acidic aqueous solutions. Because of this, it is useful as a thickening, suspending, emulsifying, stabilizing, lubricating, film-forming, or binding agent in various applications.

A particularly valuable utility is in the field of petroleum well treating fluids. Heteropolysaccharide S-421 has been found to be particularly useful in aqueous media especially formulated for use as an acidizing fluid.

The term "acidizing fluids" comprises, for example, stimulation fluids (hydraulic fracturing, matrix acidizing and acid fracturing) and other enhanced oil recovery fluids. Materials which may be present in such fluids include principally the heteropolysaccharide, an acid, preferably a non-oxidizing acid, and water. Acids used include hydrochloric acid, hydrofluoric acid, acetic acid, formic acid, or combinations thereof. It will be appreciated that the components and concentrations of any particular fluid will be selected by the well operator in the amount necessary for the particular task to be performed, however, hydrochloric acid is the predominant acid used. Acidizing fluids are prepared, for example, by diluting concentrated hydrochloric acid (28–35%) with water to the desired concentration. The heteropolysaccharide is hydrated either in diluted acid, or more preferably, in water, and then mixed with the acid.

It is recognized that the acidizing fluids of the present invention may additionally contain corrosion inhibitors, de-emulsifying agents, sequestering agents, surfactants, friction reducers, etc., known in the art. Propping agents may also be included in the fluids of the invention if desired. Propping agents that can be used include any of those known in the art, e.g. sand grains, sintered bauxite, and similar materials.

Heteropolysaccharide S-421 is usable in the acidizing fluids of the present invention in the range of 0.01% to 2.0% by weight heteropolysaccharide. The acid is usable in the acidizing fluids of the present invention in the range of about 6 to about 35% by weight, preferably from about 10 to about 28% by weight.

DESCRIPTION OF THE STRAIN

Heteropolysaccharide S-421 may be prepared by fermentation of a suitable nutrient medium with a microorganism which is an unidentified *Agrobacterium* species. A deposit under the Budapest Treaty of a biologically pure culture of the microorganism employed in making this heteropolysaccharide was made with the American Type Culture Collection, Rockville, Md., on Dec. 19, 1985 under Accession No. ATCC 53378.

A. CHARACTERISTICS OF COLONY MORPHOLOGY

On nutrient agar, a translucent colony appears in 72 hours at 30° C. with a diameter reaching about 2.0 mm in diameter. The colony was round, smooth, convex, glistening and white in color.

B. CHARACTERISTIC OF CELL MORPHOLOGY

On nutrient agar at 30° C., the organism appeared vacuolated. It was a pleomorphic, gram-negative rod with dimensions of about $0.5 \times 10$ μm. Flagella were a mix of peritrichous and polar.

C. PHYSIOLOGICAL AND BIOCHEMICAL CHARACTERISTICS

This organism grew at 30°, 37°, and 40° C. It did not grow at 43° C., nor did it grow at 4°–5° C. On triple sugar iron agar, the slant had an alkaline reaction but there was no change in the butt. There was no $H_2S$ or gas produced.

The organism was cytochrome oxidase positive and the O/F test indicated that it was oxidative. It did not grow anaerobically. There was no change in litmus milk with this organism. It was indole, methyl red, and Voges Proskauer negative. It could use citrate as a sole source of carbon and energy. It did not reduce nitrates. It used ammonia as a sole nitrogen source. It produced $H_2S$ and was urease positive. It could grow in 3% NaCl, but not in 6% NaCl. As is characteristic of *Agrobacterium radiobacter* and *Agrobacterium tumefaciens*, the isolate produced 3-ketolactose. It partially hydrolyzed gelatin, but id did not hydrolyze starch, casein, esculin, or Tween 80 (a surface active agent supplied by ICI United States, Inc., Wilmington, Del.).

There was acid production from the following carbohydrates: adonitol, lactose, raffinose, arabinose, levulose, rhamnose, dextrose, maltose, salicin, dulcitol, mannitol, sucrose, galactose, mannose, sorbitol, inositol, melibiose, trehalose, xylose.

No acid was produced from inulin.

D. IDENTIFICATION

Certain *Agrobacterium* can infect plants and cause crown gall tumors that grow undifferentiated at the site of infection. In fact, R. E. Buchanan and N. E. Gibbons, eds. *Bergey's Manual of Determinative Bacteriology*, Williams and Wilkins, Baltimore (1974) p. 265, distinguished the species *Agrobacterium tumefaciens* from *Agrobacterium radiobacter* by virtue of tumorigenic activity. More recently, it was discovered that the tumor inducing agent is a plasmid (the Ti-plasmid) that integrates some of its DNA into the host cell chromosome of the infected plant. *Agrobacterium* that lack the Ti-plasmid do not induce crown gall disease and, except for this tumor producing ability, there is no known morphological, physiological, or genotypic difference between *Agrobacterium radiobacter* and *Agrobacterium tumefaciens*.

In order to devise a scheme for the identification and differentiation of *Agrobacterium*, it was proposed that tumorigenic strains should not be considered different species but as different pathovors since, in part, these Ti-plasmids could be easily lost by the microorganisms in nature or in the laboratory. See Holmes, B. and Roberts, P., *J. Appl. Bacteriol.*, 50 (3) (1981) pp. 443–468. Consequently, S-421, ATCC 53378, was not tested for tumorigenic activity and was classified as an unidentified *Agrobacterium* species on the basis of its morphological, physiological and biochemical characteristics and on the basis of the production of the acid stable heteropolysaccharide S-421. N. R. Krieg, ed. *Bergey's Manual of Systematic Bacteriology*, Williams and Wilkins, Baltimore (1984), p. 249, however, still classifies *Agrobacterium* on the basis of tumorigenicity.

Other embodiments of the present invention will be apparent to one skilled in the art from a consideration of this specification. It is intended, therefore, that the specification and examples be considered as exemplary only, with the true scope and spirit of the invention being indicated by the following claims.

EXAMPLE 1

Effect of Media on Gum Production

A YM flask seed was started from a 48-hour nutrient agar culture placed on a gyrotary shaker at 30° C. Approximately, 24 hours later this seed was used to inoculate a flask containing $E_1$ medium with 3% hydrolyzed starch as the carbon source. This medium was also placed on a gyrotary shaker at 30° C. Approximately 72 hours later, this flask was noted to have viscous beer, and upon addition of 2 volumes of 99% isopropyl alcohol, a fibrous precipitate was noted.

$E_1$ medium contains 5 g of dipotassium phosphate, 0.1 g of magnesium sulfate, 0.9 g of ammonium nitrate, 0.5 g of Promosoy 100 (an enzymatic digest of soybean meal sold by Central Soya Chemurgy Division), 30 g of dextrose and 1 L of tap water. The pH of the $E_1$ medium is about 7.6–7.8.

Another YM seed flask was prepared in the above fashion and used at 24 hours to inoculate 5 flasks containing various media and these flasks were incubated at 30° C. on a gyrotary shaker for about 72 hours at which time the pH, viscosity, gum yield and product viscosity were measured. The results are shown in Table 2 below.

TABLE 2

| Medium | Carbon Source | pH | Beer Vis (cP) | % Gum Yield |
|---|---|---|---|---|
| $E_1$ | 3% hydrolyzed starch | 7.4 | 10 | 0.00 |
| $E_1$ (—NH$_4$NO$_3$ + 0.19% NaNO$_3$) | 3% hydrolyzed starch | 7.9 | 25 | 0.60 |
| $E_1$ (containing 0.2% Promosoy 100 | 3% hydrolyzed starch | 7.7 | 15 | 1.09 |
| $E_1$ | 3% glucose | 7.6 | 230 | 0.70 |
| $E_1$ + HoLe Salts[1] | 3% hydrolyzed starch | 7.8 | 15 | 1.07 |

[1]HoLe salts: An aqueous solution (used at 1 ml/L of medium) comprising

| | Conc. In Final Medium (ppm) |
|---|---|
| H$_3$BO$_3$ | 0.05 B$^{+3}$ |
| MnCl$_2$.4H$_2$O | 0.5 Mn$^{+2}$ |
| FeSO$_4$ | 0.5 Fe$^{+2}$ |
| CuCl$_2$ | 0.01 Cu$^{+2}$ |
| ZnCl$_2$ | 0.02 Zn$^{+2}$ |
| CoCl$_2$.6H$_2$O | 0.01 Co$^{+2}$ |
| Na$_2$MoO$_4$.2H$_2$O | 0.01 Mo$^{+6}$ |
| Sodium Tartrate | 1.8 |

EXAMPLE 2

Additional Study of Effect of Media on Gum Production

Based on the results of Example 1, another YM seed flask was prepared in the manner described therein and was used to inoculate five flasks containing various media, but in which 3% glucose was the carbon source used in the majority of flasks. These flasks were incubated on a shaker at 30° C. for about 72 hours at which time the pH, viscosity, gum yield and product viscosity were measured. The results are shown in Table 3 below.

TABLE 3

| Medium | Carbon Source | pH | Beer Vis (cP) | Gum Yield (%) |
|---|---|---|---|---|
| $E_1$ | 3% glucose | 7.4 | 245 | 0.70 |
| $E_1$ (—NH$_4$NO$_3$ + 0.19% NaNO$_3$) | " | 7.3 | 65 | 0.40 |
| $E_1$ + 0.2% promosoy | " | 6.6 | 2300 | 1.55 |
| $E_1$ | 3% hyd. starch | 7.7 | 40 | 1.24 |
| $E_1$ + HoLe Salts | 3% glucose | 6.5 | 2100 | 1.28 |

The results indicated that $E_1$ containing 0.2% promosoy and 3% glucose was the best growth medium.

EXAMPLE 3

Optimum Medium for S-421

The results of an S-421 media screening experiment show that the addition of manganese stimulates the fermentation but the best results were obtained with the addition of Hole salts.

Results of the Experiment (harvested at 120 hrs)

| Media | pH | Vis (cP) | Residual Carbon Source (%) | Yield % | Syn Tap H$_2$O 1% | Vis (cP) 0.1% |
|---|---|---|---|---|---|---|
| 1. $E_{-1}$ | 7.2 | 810 | 0.95 | 0.78 | | |
| 2. $E_1$ + Hole salts | 7.2 | 3000 | 0.02 | 1.47 | 1540 | 56 |
| 3. 1 + B$^{++}$ | 7.2 | 1270 | 0.47 | 1.08 | 1220* | 26 |
| 4. 1 + Mn$^{++}$ | 7.2 | 2300 | 0.02 | 1.23 | 1380 | 51 |
| 5. 1 + Fe$^{++}$ | 7.4 | 820 | 0.48 | 0.85 | | |
| 6. 1 + Cu$^{++}$ | 7.4 | 820 | 0.92 | 0.79 | | |
| 7. 1 + Zn$^{++}$ | 7.4 | 780 | 0.94 | 0.86 | | |
| 8. 1 + Co$^{++}$ | 7.4 | 530 | 0.97 | 0.67 | | |
| 9. 1 + Mo$^{++}$ | 7.4 | 700 | 0.95 | 0.76 | | |
| 10. 1 + Tartrate | 7.4 | 860 | 0.92 | 0.89 | | |

*very foamy

Two experiments were conducted in 14 L fermentor vessels in the following medium:
3% Glucose
0.05% Promosoy 100
0.01% MgSO$_4$.7H$_2$O
0.09% NH$_4$NO$_3$
0.005% SAG 5693 (a antifoam agent supplied by Union Carbide)
1 ppm Fe$^{++}$ (added as FeSO$_4$.7H$_2$O)
8 ppm Mn$^{++}$ (added as MnCl$_2$.4H$_2$O)
Tap Water The K$_2$HPO$_4$ concentration was varied from 0.05–0.50% in the first experiment and from 0.25–0.35 in the second experiment. A 0.1% product viscosity of $\geq$40 cP was required to established an improvement in growth medium. The results show that the phosphate concentration influences final product viscosity and that a K$_2$HPO$_4$ concentration of 0.25% in the medium would product product with viscosities $\geq$40 cP.

| Experiment No. | K$_2$HPO$_4$ Concentration (%) | Fermentation Time (hrs.) | Gum Yield (gm %) | 0.1% Viscosity (CP) |
|---|---|---|---|---|
| 1 | 0.05 | 190 | 1.38 | 34 |
| | 0.20 | 211 | 1.51 | 58 |
| | 0.35 | 139 | 1.55 | 53 |
| | 0.50 | 139 | 1.97 | 32 |
| 2 | 0.25 | 64 | 1.42 | 41 |

-continued

| Experiment No. | $K_2HPO_4$ Concentration (%) | Fermentation Time (hrs.) | Gum Yield (gm %) | 0.1% Viscosity (CP) |
| --- | --- | --- | --- | --- |
| | 0.35 | 113 | 1.29 | 35 |

EXAMPLE 4

Fermentation Procedure for Producing Large Quantities of Heteropolysaccharide S-421

A 500 ml flask containing 100 ml of YM (Difco) broth was inoculated with a loopful of *Agrobacterium* sp. culture, ATCC 53378, from a 48-hour nutrient agar plate. After incubation with shaking for 24 hours at 30° C., a 5% transfer was made from this YM seed into a 200 ml volume of $E_1$. medium with HoLe salts and 3% glucose. After a similar incubation period, this seed was used to inoculate a five-liter fermentor containing 2.8 L of the following medium:

3.0% Glucose
0.5% $K_2HPO_4$
0.05% Promosoy ®100
0.01% $MgSO_4.7H_2O$
0.09% $NH_4NO_3$
0.005% SAG 5693 (an antifoam agent supplied by Union Carbide)
1 ml/L HoLe Salts
1 ppM $Fe^{++}$ (added as $FeSO_4.7H_2O$)
Tap Water The temperature was maintained at 30° C. and the aeration at 1 L/M. The agitation was started at 400 RPM and increased thereafter to ensure good mixing. At 24 hours, approximately 2.5 L of this seed was used to inoculate a 70 L fermentor containing a final medium volume of 50 L. The medium was as follows:

3.0% Glucose
0.25% $K_2HPO_4$
0.05% Promosoy 100
0.01% $MgSO_4.7H_2O$
0.09% $NH_4NO_3$
0.005% SAG 5693
1 ml/L HoLe Salts
1 ppm $Fe^{++}$ (added as $FeSO_4.7H_2O$)
Tap Water The temperature was maintained at 30° throughout the fermentation. The fermentation was started with 10 L/M of air and 300 RPM agitation. The pH was controlled at 6.8 by the addition of 40% KOH as needed using an automatic pH control system. The agitation was increased as necessary to ensure good mixing. The aeration was increased to 20 L/M at 24 hours and remained at that rate for the rest of the fermentation. The results of the fermentation are given below:

| Age (hrs) | pH | Beer Viscosity (cP) | Gum Yield (%) | Residual Carbon Source (%) |
| --- | --- | --- | --- | --- |
| 0 | 7.33 | — | — | 3.0 |
| 18½ | 6.9 | — | — | — |
| 44½ | 6.7 | 840 | — | — |
| 66½ | 6.5 | 1420 | 1.167 | 0.547 |
| 90 | 6.4 | 1670 | 1.40 | 0.20 |

The fermentation liquor was heated to approximately 75° C. for 15 minutes and then cooled to 30° C. The fermentation liquor was then added to approximately two volumes of 99% isopropanol. The heteropolysaccharide precipitated as a fibrous material which was easily recovered with a sieve. The fibers were dried in a forced air tray drier at 55° C. for approximately 45 minutes before being milled to a powder. When reconstituted in synthetic tap water at 0.1% concentration, the viscosity was 52 cP (UL Adapter, Broofield LVF viscometer, 6 RPM).

EXAMPLE 5

Initial Viscosity of Heteropolysaccharide S-421

The initial viscosity of S-421 was determined by the following procedure. The polymer was first hydrated in tap water at a concentration of 2% (6 g in 300 ml) by mixing for 30 minutes on a Hamilton Beach mixer (model 936) at 100% speed. To a suitable jar were added 0.2 ml of a corrosion inhibitor, an appropriate amount of polymer concentrate, additional water to achieve the desired polymer concentration in the acid fracturing fluid, and finally concentrated hydrochloric acid. The fluid was mixed for two minutes at fairly low agitation rates to ensure homogeneity. As an example, a fluid consisting of 15% HCl and 1.25 lb polymer/barrel was made from 54 g of the polymer concentrate, 136 ml water, and 110 ml concentrated hydrochloric acid. A Fann 35 viscometer was then used to measure sample viscosity at 3 rpm, results of which are shown below:

| | INITIAL VISCOSITY | | |
| --- | --- | --- | --- |
| Polymer | Polymer Conc. (%) | % HCl | Viscosity (cP) |
| S-421 | 0.36–0.60 | 15 | 590–1460 |
| " | 0.36–0.60 | 20 | 550–1480 |
| " | 0.43–0.60 | 22 | 500–1760 |
| " | 0.43–0.60 | 24 | 400–1640 |
| " | 0.43–0.60 | 26 | 400–1590 |
| " | 0.47–0.60 | 28 | 240–960 |

EXAMPLE 6

Viscosity Half Life of Heteropolysaccharide S-421

The viscosity half-life, defined as the time to lose half the initial viscosity on a Fann 35 Viscometer at 3 RPM, was measured for heteropolysaccharide S-421. The results show that heteropolysaccharide S-421 thickened acid solutions have long viscosity half-life even at high temperatures. Longer viscosity half-life translates into longer HCl spending rates. The results are presented below:

| VISCOSITY HALF-LIVES[1] OF HETEROPOLYSACCHARIDE S-421 | | | | | | | |
| --- | --- | --- | --- | --- | --- | --- | --- |
| Storage Temperature (°F.) | % HCl | | | | | | |
| | 10 | 15 | 20 | 22 | 24 | 26 | 28 |
| 75 | 2 hr. | 2 hr. | 2 hr. | 2 hr. | 2 hr. | 2 hr. | 2 hr. |
| 100 | N.D. | 2 hr. | 2 hr. | 2 hr. | 1.0 hr. | 0.75 hr. | ≠ |
| 125 | 2 hr. | 1.5 hr. | 0.5 hr. | 0.5 hr. | 0.5 hr. | 0.25 hr. | ≠ |
| 150 | N.D. | 0.25 hr. | N.D. | 0.25 hr. | N.D. | N.D. | N.D. |
| 175 | 0.5 hr. | N.D. | N.D. | N.D. | N.D. | N.D. | N.D. |

[1]Viscosity half-lives were not determined beyond two hours because longer half-lives are not necessary for acid fracturing applications.
N.D. = not determined
≠ = Initial viscosity too low to determine viscosity half-lives.

EXAMPLE 7

HCl Spending Rate of Heteropolysaccharide S-421

During acid fracturing, it is desirable to retard the neutralization process until the acid solution has deeply penetrated the underground formation. Thus, a study was made of the effect of heteropolysaccharide S-421 on the spending rate of HCl (rate of neutralization) in the presence of $CaCO_3$ marble chips.

In the test procedure, 80 g of marble chips were added to 200 ml of a 15% HCl solution containing (a) no polysaccharide and (b) 1.25 ppb heteropolysaccharide S-421. The acid solution was held at 75° F. and at time intervals of 0, 3, 6, 12, 24, and 48 minutes a sample was drawn and titrated against a 0.1N NaOH solution. The experiment was repeated except that the acid solution was held at 125° F. The results are shown below:

|  | Time (minutes) | % HCl (75° F.) | % HCl (125° F.) |
| --- | --- | --- | --- |
| S-421 | 0 | 14.9 | 14.8 |
|  | 3 | 10.1 | 8.2 |
|  | 6 | 7.6 | 5.8 |
|  | 12 | 6.9 | 5.9 |
|  | 24 | 6.3 | 4.4 |
|  | 48 | 5.3 | 3.2 |
| No polymer | 0 | 14.7 | 14.8 |
|  | 3 | 2.8 | 2.9 |
|  | 6 | 0.4 | 0.3 |
|  | 12 | 0 | 0 |
|  | 24 | 0 | 0 |
|  | 48 | 0 | 0 |

The results show that acid solutions containing heteropolysaccharide S-421 have significantly longer spending rates (slower rates of acid neutralization) than acid solutions containing no polymer.

What is claimed is:

1. An aqueous acidizing fluid which comprises from about 6 to about 35% by weight acid and from about 0.1 to about 2.0% by weight heteropolysaccharide S-421, said heteropolysaccharide S-421(a) containing principally carbohydrate, about 12% by weight protein, about 4% by weight acyl groups principally as O-succinyl groups, and about 4% by weight pyruvate, said carbohydrate portion containing the neutral sugars glucose and galactose in the approximate molar ratio of 6:1 and (b) prepared by a process comprising growing the *Agrobacterium* species ATCC 53378 in an aqueous nutrient medium by aerobic ferementation of an assimilable carbon source.

2. The fluid of claim 1, wherein the acid is a non-oxidizing acid.

3. The fluid of claim 2, wherein the acid is selected from the group consisting of hydrochloric acid, hydrofluoric acid, acetic acid, and formic acid.

4. The fluid of claim 3, wherein the acid is hydrochloric acid.

5. The fluid of claim 4, which comprises from about 10 to about 28% by weight hydrochloric acid.

* * * * *